(12) United States Patent
Heiss

(10) Patent No.: US 11,406,486 B2
(45) Date of Patent: *Aug. 9, 2022

(54) SUCTION STENT, STENT SYSTEM, AND METHOD FOR SEALING A LEAKAGE

(71) Applicant: Vac Stent Medtec AG, Zug (CH)

(72) Inventor: Markus M. Heiss, Cologne (DE)

(73) Assignee: Vac Stent Medtec AG, Zug (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/997,690

(22) Filed: Aug. 19, 2020

(65) Prior Publication Data

US 2020/0375718 A1    Dec. 3, 2020

Related U.S. Application Data

(60) Continuation of application No. 16/035,120, filed on Jul. 13, 2018, now Pat. No. 10,779,928, which is a
(Continued)

(51) Int. Cl.
*A61F 2/04* (2013.01)
*A61F 2/82* (2013.01)
(Continued)

(52) U.S. Cl.
CPC ............ *A61F 2/04* (2013.01); *A61B 17/0057* (2013.01); *A61B 17/1114* (2013.01); *A61F 2/945* (2013.01); *A61M 1/0001* (2013.01); *A61M 1/90* (2021.05); *A61B 2017/00659* (2013.01); *A61F 2/07* (2013.01); *A61F 2002/045* (2013.01); *A61F 2002/077* (2013.01); *A61F 2002/823* (2013.01); *A61F 2210/0085* (2013.01);
(Continued)

(58) Field of Classification Search
CPC ........ A61F 2/04; A61F 2/07; A61F 2002/045; A61F 2002/077; A61F 2002/823; A61F 2250/0069; A61F 2250/0003; A61F 2230/0078; A61B 17/0057
See application file for complete search history.

(56) References Cited

U.S. PATENT DOCUMENTS 5,078,704 A    1/1992  Wejnar
5,876,448 A    3/1999  Thompson et al.
(Continued)

FOREIGN PATENT DOCUMENTS

EP    1633279 B1    2/2011
WO    2003028522 A2    4/2003
(Continued)

*Primary Examiner* — Dinah Baria
(74) *Attorney, Agent, or Firm* — Dinsmore & Shohl LLP

(57) ABSTRACT

A suction stent for introduction into a hollow organ of the human or animal body, preferably into the gastrointestinal tract, in particular the intestine, includes a tubular hollow body which is open in the longitudinal direction and made of biocompatible material. The tubular hollow body has a fixed diameter at least in its central portion; and a porous shapeable material, preferably a sponge material, which is biocompatible and shapeable in the radial direction, the porous shapeable material radially sheathing the tubular hollow body at least in a section of the tubular hollow body. Further, a method is provided for sealing a leakage, especially an anastomosis, of the hollow organ.

25 Claims, 12 Drawing Sheets

Related U.S. Application Data division of application No. 15/103,923, filed as application No. PCT/EP2013/003768 on Dec. 13, 2013, now Pat. No. 10,058,413.

(51) Int. Cl.
| | | |
|---|---|---|
| *A61M 1/00* | (2006.01) | |
| *A61F 2/945* | (2013.01) | |
| *A61B 17/00* | (2006.01) | |
| *A61B 17/11* | (2006.01) | |
| *A61F 2/07* | (2013.01) | |

(52) U.S. Cl.
CPC ............. *A61F 2230/0078* (2013.01); *A61F 2250/0003* (2013.01); *A61F 2250/0069* (2013.01); *A61M 1/0003* (2013.01); *A61M 2210/105* (2013.01); *A61M 2210/106* (2013.01); *A61M 2210/1064* (2013.01)

(56) References Cited

U.S. PATENT DOCUMENTS

| | | |
|---|---|---|
| 8,007,541 B2 | 8/2011 | Benz et al. |
| 8,858,612 B2 | 10/2014 | Ben-Muvhar et al. |
| 2006/0095124 A1 | 5/2006 | Benz et al. |
| 2007/0233227 A1 | 10/2007 | Greenan |
| 2007/0275156 A1 | 11/2007 | Tanaka et al. |
| 2007/0282453 A1 | 12/2007 | Weitzner et al. |
| 2010/0174381 A1 | 7/2010 | Benz et al. |
| 2012/0130467 A1* | 5/2012 | Selden .............. A61L 31/148 623/1.2 |

FOREIGN PATENT DOCUMENTS

| | | |
|---|---|---|
| WO | 2003096932 | 11/2003 |
| WO | 2007142833 A1 | 12/2007 |

* cited by examiner

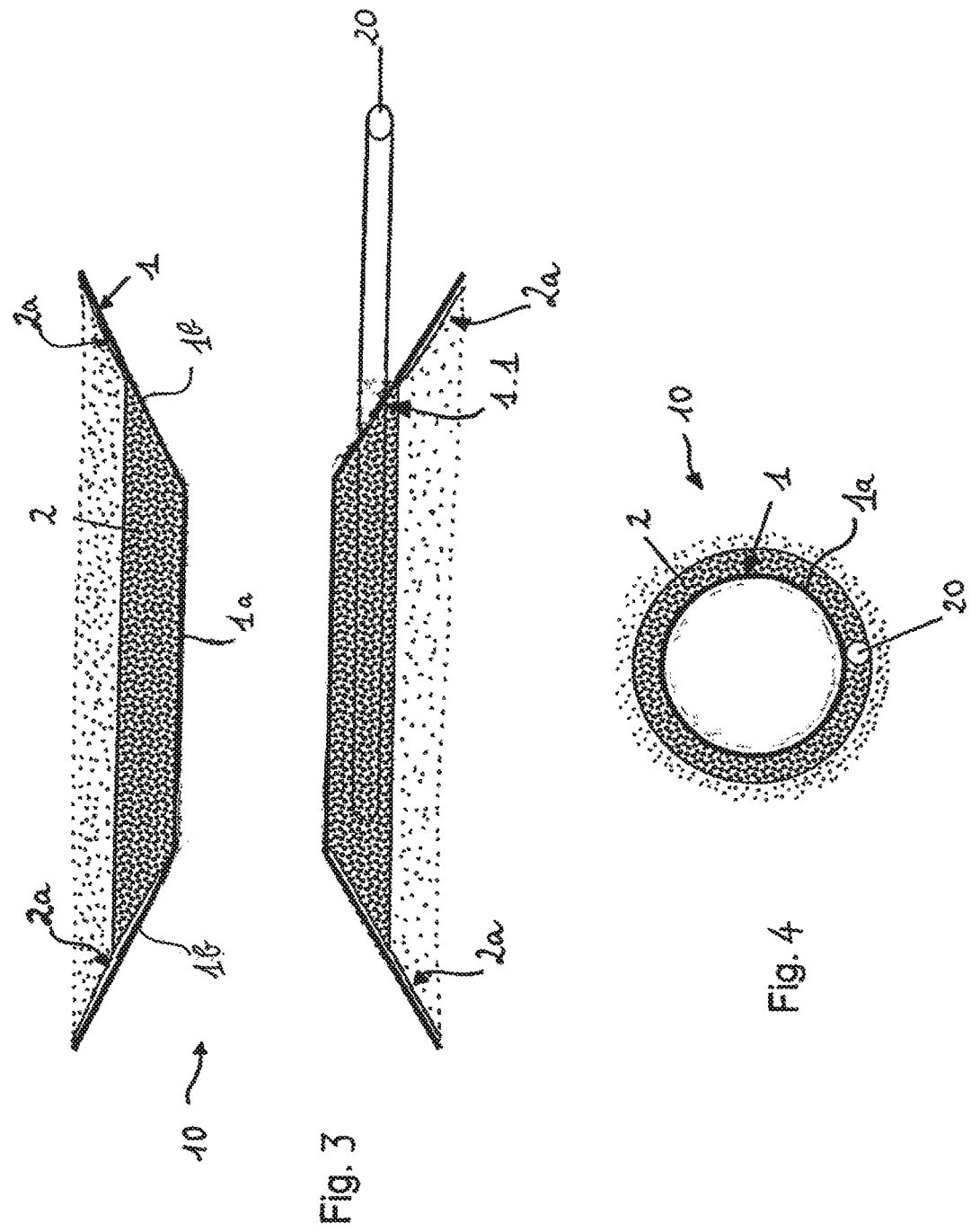

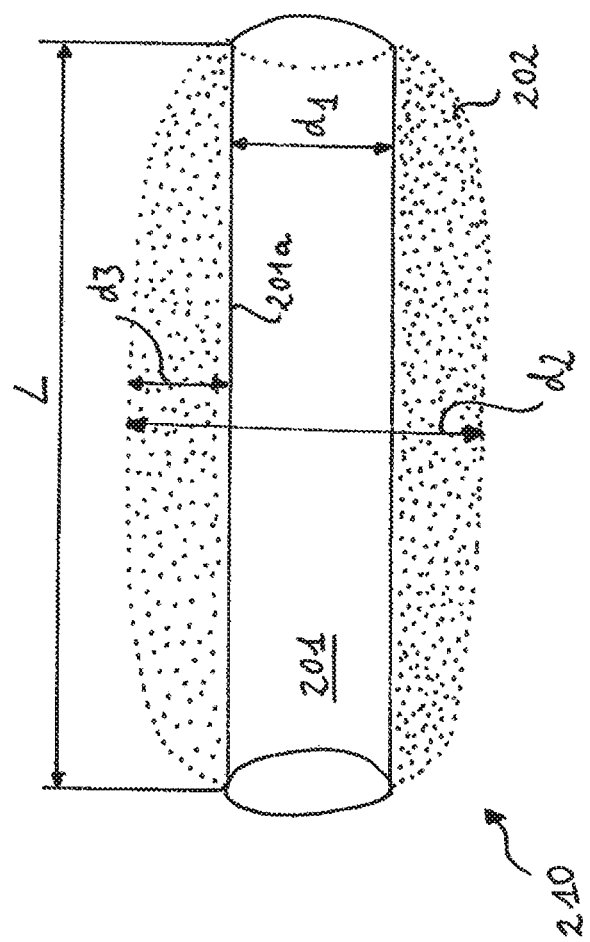

SUCTION STENT, STENT SYSTEM, AND METHOD FOR SEALING A LEAKAGE

CROSS-REFERENCE TO RELATED APPLICATIONS

This application is a Continuation of U.S. patent application Ser. No. 16/035,120, filed Jul. 13, 2018, which is the divisional application of U.S. patent application Ser. No. 15/103,923, filed on Jun. 13, 2016, which is the U.S. national stage of PCT/EP2013/003768 filed Dec. 13, 2013. The entire content of each application is incorporated herein by reference.

FIELD OF THE INVENTION

The present invention relates to a suction stent according to claim 1 as well as to a method for sealing a leakage according to the respective independent method claim.

BACKGROUND OF THE INVENTION

In the field of stents for introduction in hollow organs, especially in context with the intestine, there is the need to provide a reliable device and method for sealing a defect (e.g. an anastomosis) in a wall of the organ.

EP 1 633 279 B1 describes a stent which is arranged to promote wound closure by exerting a radial force on the inner wall of an organ of a patient, the stent being provided with a radially expandable tubular hollow body which is coated by a porous material, e.g. a foam or a kind of sponge. The tubular hollow body exerts a radial force component on the inner wall.

SUMMARY OF THE INVENTION

It is one object of the present invention to provide a simple and/or robust stent for wound closure. It is also an object of the present invention to provide an inexpensive stent for wound closure which is composed of inexpensive and robust components. It is a further object of the present invention to provide a suction stent for wound closure with which the wound can be sealed resp. obturated (occluded) in a reliable way. It is a further object of the present invention to provide a suction stent for wound closure with which a contact pressure of a wall of an organ of a patient can be adjusted easily. It is a further object of the present invention to provide a suction stent which can be introduced in a hollow organ in an easy and reliable way. It is a further object of the present invention to provide a method for sealing a leakage in an easy and reliable way.

At least one of the above mentioned objects is attained by a suction stent for introduction into a hollow organ of the human or animal body, preferably into the gastrointestinal tract, in particular the intestine, comprising:
- a tubular hollow body which is open in the longitudinal direction and made of biocompatible material, the tubular hollow body having a fixed diameter at least in its central portion; and
- a porous shapeable material, preferably a sponge material, which is biocompatible and shapeable in the radial direction, the porous shapeable material radially sheathing the tubular hollow body at least in a section of the tubular hollow body.

By such a stent, the pressure ratio can be inversed. Instead of exerting a radial force by the stent itself, the present invention allows the wall of an organ of a patient, e.g. the intestinal wall, to ensure wound closure. If desired, such a stent may remain several days within the body. In particular, the stent may remain for up to 10 days implemented within the body. The pressure between the stent and the organ is not provided via a tubular hollow body exerting a radial force outwardly, but via the wall of the hollow organ itself. Thereby, the porous shapeable material itself is arranged for exerting a sufficiently high radial force on the hollow organ in order to ensure that the inner wall of the hollow organ snuggles to its outer surface, especially by adapting its diameter to the geometry of the hollow organ.

The stent can be implemented as a prophylactic, preventive stent (e.g. in context with unstable, labile seams) or as a permanent stent (permanently remaining in the body), especially post-operatively, i.e. in a post-surgery context.

With a suction stent according to the invention, there is no need of a (further) radial force component provided by e.g. any expandable tubular hollow body. A radial reaction force of the porous shapeable material was found to be sufficient in order to ensure sealing of e.g. an anastomosis. The radial force of the porous shapeable material corresponds to a reaction force which is due to a radial force directed inwardly and exerted by the wall of the organ, e.g. the intestine. As the porous shapeable material itself can ensure sealing, in a second step, a vacuum drainage may be applied easily to the porous shapeable material in order to provide a subnormal pressure between the organ and the tubular hollow body. Depending on the material of the porous shapeable material, in order to ensure sealing of the wall of the organ, suction by subnormal pressure can ensure that the inner organ's wall, typically its epithelium forming the inner wall, is sucked against the porous shapeable material. Thereby, the inner wall may be sealed in an air-tight and watertight manner. By applying subnormal pressure by suction, infectious secretion may additionally be pumped out via the vacuum drainage.

In other words, the concept of the present invention is based on the surprising finding resp. recognition that there is no need for any tubular hollow body exerting a radial force outwardly. Rather, a radial force resp. a kind of radial counterpressure or radial resistance caused solely by the porous shapeable material is sufficient to ensure sealing. If desired, the effect may be combined with applying a subnormal pressure exerted by drainage means.

The porous shapeable material may be provided in the form of a sponge or foam. According to one alternative, the porous shapeable material is a plastics material foam, especially a polyurethane or a polyvinyl alcohol. In one preferred embodiment, the porous shapeable material is a silicone sponge.

The porous shapeable material can be provided open-pored or with closed pores. Preferably, an open-pored structure to be used has 20 to 40 pores per 1 inch, especially at least approximately 30 pores. A strain-hardness is preferably in the range of 2 to 10 kPa, especially about 5 kPa, especially at a compression of about 40%. Preferably, the porous shapeable material is a sponge which is based on or consists of polyurethane or polyester material, or co-polymers thereof. According to one alternative, the porous shapeable material may be based on polyurethane which itself is based on polyester. According to another embodiment, the porous shapeable material may be an open-pored silicon sponge. Silicon material is highly inert and resistant. Alternatively, the porous shapeable material can be provided in the form of a gauze.

Preferably, the porous shapeable material is fixed directly at the outer surface of the tubular hollow body. Fixation may be achieved e.g. by adhesion or simply by the material's self-contracting properties. E.g., the porous shapeable material can be attached to the outer surface or pulled over the outer surface of the tubular hollow body.

Preferably, the tubular hollow body is incompressible (with respect to the pressure conditions within a human or animal body) in the radial direction over its entire length or at least within a section. Inexpandabability and/or incompressibility are typically realized in its central portion. As the tubular hollow body of the stent does not have to be compressible and/or radially expandable, a simple tube or pipe of a rigid material or of a material which is not deformable in the radial direction can be used, e.g. a silicone tube. It is further preferred that the tubular hollow body is provided with a coherent (self-contained) circumferential inner wall, i.e. without any holes or perforations or openings (apart from any point of passage for drainage means, if required).

Also, due to a coherent (self-contained) tubular hollow body, for applying a vacuum, an airtight foil between the porous shapeable material and any grid-structured tubular hollow body is not required any more, as the tubular hollow body according to the invention can be provided itself as an airtight hose or tube or pipe. Thereby, the manufacturing costs for a stent according to the invention can be considerably reduced, especially of compared prior art stents provided in the form of a radially expandable grid structure. Also, a catheter for placing the stent within an organ, especially within the intestine, can be designed without the need to hold/secure any radially expandable grid structure at a smaller diameter prior to its placement. The dimensions of the stent can essentially be adapted to the size of a catheter resp. endoscope. In particular, the inner diameter of the stent can be chosen to be relatively large, as the inventive stent is not surrounded by layers of significant thickness in the radial direction (other than a layer of the porous shapeable material of e.g. 1 to 5 mm). In other words, the wall thickness of the stent is reduced. As already mentioned, an air- and/or water-tight film between the tubular hollow body and the porous shapeable material does not need to be provided any more, if the hollow body is made of e.g. an air- and watertight hose, tube or pipe. It may, however, be provided at certain portions of the inventive stent, e.g. the terminal portions and/or in the central portion, if required.

Further, the stent according to the invention provides physiological advantages, as there is no expandable tubular hollow body exerting a high radial pressure on the organ. Thus, the radial pressure exerted on the organ can be adjusted in a more flexible way by the vacuum itself: the contacting force between the inner wall of the organ and the porous shapeable material is the result of the pressure difference between the patient's pressure conditions at the implantation site and the subnormal pressure applied.

According to one embodiment of the invention, the tubular hollow body of essentially cylindrical shape is a pipe or tube having an inner diameter allowing passage of body fluids through its lumen. It is flexible, especially elastically bendable, with respect to its longitudinal axis. In other words, the tubular hollow body does not necessarily have to be completely rigid in order to fulfill its function when implanted, in particular when pressure is applied. Rather, it may be preferred, if the tubular hollow body is flexible for facilitating its implantation within the organ, especially the intestine which may have a curved geometry at the site of implantation.

Preferably, the tubular hollow body is provided in the form of a cylinder with a cylindrical geometry at least at a central portion of the tubular hollow body, wherein one or both end portions (or faces resp. front sides) of the tubular hollow body may deviate from the cylindrical form. Preferably, the tubular hollow body is provided with a continuous (inner and/or outer) surface which does not have any openings or holes, especially a circumferential cohesive (coherent) inner surface. According to one embodiment, the porous shapeable material is provided cylindrically around the tubular hollow body only in a central portion, at least section-wise. Thereby, at its end portions resp. faces resp. front sides, the porous shapeable material can be provided with a canted or slanted geometry. Further, the porous shapeable material can slightly deviate from a strict cylindrical shape, also with respect to a central portion. E.g., the porous shapeable material can be provided in a slightly elliptical shape.

According to one embodiment of the invention, the porous shapeable material is provided over at least 50% of the extension (length) of the tubular hollow body in its longitudinal direction. Preferably, the tubular hollow body is covered by the porous shapeable material over at least 75% of its extension (length). Hereby, the tubular hollow body can be handled easily, and the main portions of the tubular hollow body are covered by the porous shapeable material. Covering at least most of the tubular hollow body provides the advantage that the organ is not in contact with any rigid portions of the stent. A porous shapeable material which is not provided over the full extension of the tubular hollow body provides the advantage that the tubular hollow body can direct any intestinal secretions via the lumen of the tubular hollow body. In other words, the porous shapeable material is prevented from being occluded by any intestinal secretions resp. fluids or particles. Preferably, the porous shapeable material is provided maximally over 90% of the longitudinal dimension of the tubular hollow body, in particular, the end portions of the tubular hollow tube may not be covered by the porous shapeable material. A tubular hollow body protruding from the porous shapeable material can ensure the radial flexibility of the porous shapeable material. By another embodiment, the porous shapeable material extends over the entire length of the tubular hollow body. In this embodiment, it is preferred that the thickness of the porous shapeable material decreases in the vicinity of the end portions of the tubular hollow body.

According to one embodiment of the invention, the tubular hollow body is impermeable to water or to water and gas respectively air. Hereby, a subnormal pressure can be applied to the porous shapeable material and the inner wall of the hollow organ without the need of any water- and/or air-tight foils.

According to one embodiment of the invention, the tubular hollow body may be provided such that it is radially expandable in one or both peripheral (terminal) sections of the tubular hollow body, especially at one or both end portions of the tubular hollow body, with the central portion (e.g. up to 70% of the entire longitudinal dimension) being inexpandable. For a tubular hollow body which is expandable in a peripheral portion only, a funnel-shaped geometry can be realised. An expansion in a peripheral portion of the hollow body does not affect the pressure conditions at the anastomosis, as the stent is implanted such that the peripheral portions are in contact with the tissue proximal or distal to the site of implantation, e.g. at the site of the anastomosis. A funnel-shaped geometry provides the advantage of fixation of the stent when implanted and of an enlarged luminal diameter facilitating the flow of the body fluids. Moreover, the porous shapeable material can be pulled over the outer surface of the tubular hollow body (without any further fixing). Finally, the funnel-shaped geometry ensures that the porous shapeable material does not slide down from the tubular hollow body. A stent with a porous shapeable material surrounding the tubular hollow body can be provided cost-effectively, as preferably no biocompatible adhesive is required.

The ability to radially expand in a peripheral terminal portion of the tubular hollow body (each terminal portion typically accounting for 10 to 30% of the entire longitudinal dimensions of the tubular hollow body) can be provided by a tubular hollow body which is composed of at least two different materials, wherein at least one peripheral portion is provided with a material differing from the material of a central portion. Alternatively, the tubular hollow body may be composed of only one single material (e.g. silicone) over its entire length, but with different wall thicknesses, wherein at least one peripheral portion is provided with a lower wall thickness than the central portion.

By another embodiment, the tubular hollow body is preformed in a rigid funnel-shaped geometry at one end portions (especially the distal end portion) without allowing for radial expansion. According to one embodiment of the invention, the tubular hollow body is entirely made of an inexpandable material and is provided with a funnel-shaped geometry at one or both peripheral portions of the tubular hollow body.

A funnel-shaped geometry at one or both end portions of the tubular hollow body, be it by radial expansion or due to its preformed geometry, can ensure that the front sides of the porous shapeable material do not need to be sealed, e.g. for air- and/or water-tightness, or to avoid occlusion of the shapeable material's pores by body fluids or particles. In other words: the tubular hollow body itself can ensure air- and/or water-tightness, also with respect to the longitudinal direction. A funnel-shaped geometry provides the advantage that an endoscope can easily be channelled through the tubular hollow body or passed through the tubular hollow body.

Preferably, drainage means provided for exerting a subnormal pressure pass the tubular hollow body in a funnel-shaped end portion in a point of passage. According to one embodiment, the drainage means are provided in the form of a (especially flexible) tube, wherein the point of passage is a round or elliptical opening resp. hole.

According to one embodiment of the invention, the thickness of the porous shapeable material in a discharged or relieved state is between 4 and 12 mm, preferably between 5 and 10 mm, especially about 7.5 mm. Thereby, the thickness refers to the wall thickness of the porous shapeable material cylindrically surrounding the hollow body, at least section-wise. In a compressed state, the thickness of the porous shapeable material can be between 2 and 4 mm, preferably 3 mm. In particular, a sponge consisting of e.g. polyurethane material may be compressed by up to 80% (referring to the compression in the radial dimension). Preferably, the sponge is compressible by from 30 to 80%, further preferred by at least 50 to 60%. A high compressibility in radial dimensions of the porous shapeable material provides a stent which can be introduced into the body's luminal organ in an easy way. It is favoured that the stent has the largest inner-luminal diameter possible, while it still can adapt to specific shapes of the hollow organ.

The length of the tubular hollow body can be chosen dependent on the type of the hollow organ, the medical need and further patient-specific parameters, e.g. the size of the anastomosis. The length of the tubular hollow body is preferably between 40 and 140 mm, further preferred between 60 and 80 mm, especially at least approximately about 70 mm. In particular, a length of about 70 mm provides the advantage that the stent can be introduced into the organ without evoking any specific issues in surgery, e.g. gastro-intestinal surgery.

According to one embodiment, the porous shapeable material is covered by a foil or film, which may improve the tolerance of the implant by the patient. The foil can e.g. prevent direct contact between the porous shapeable material and the inner wall of the organ, e.g. the intestinal mucosa, if there is need for such coverage, e.g. for avoiding adverse reaction by the mucosa. On the other hand, it has been found that the intestinal mucosa is usually resistant against a sponge material of commonly used materials, e.g. made of polyurethane. The material of the foil or film is preferably polyurethane, latex or silicone. The foil may be perforated.

According to one embodiment of the invention, a luminal inner diameter of the tubular hollow body is between 5 and 15 mm, preferably 6 and 12 mm. Such an inner diameter (which is relatively large) avoids any blockade of the intestine when the stent is implanted, and reduces any risk of occlusion.

According to one embodiment of the invention, an outer diameter of the porous shapeable material in a discharged resp. relieved state is between 15 and 35 mm, preferably 20 and 30 mm, especially at least approximately about 25 mm. Hereby, a stent can be provided which, in a compressed state, has quite small radial extensions. It has been found that a diameter of about 25 mm is big enough to ensure sealing.

According to one embodiment of the invention, the ratio of the outer diameter of the porous shapeable material in a discharged resp. relieved state to the luminal inner diameter of the tubular hollow body is between 3 and 7, preferably 4 and 6, especially 5. Such a ratio can ensure a relatively big inner lumen of the tubular hollow body as well as the ability of the porous shapeable material to adapt to the shape of the inner wall of the hollow organ.

According to one embodiment of the invention, the thickness of a wall of the tubular hollow body is between 0.5 and 5 mm, preferably 0.5 and 2.5 mm, especially between 1 and 2 mm. Such a (quite small) thickness can ensure a relatively big inner lumen of the tubular hollow body. Also the tubular hollow body remains flexible.

According to one embodiment of the invention, the suction stent further comprises drainage means, especially a suction hose, preferably a vacuum tube, which are fixed at or in the porous shapeable material. By drainage means directly coupled to the porous shapeable material, a subnormal pressure can be realized in the vicinity of the inner wall of the organ, especially the anastomosis. The fixation can be carried out by bonding, by sewing resp. by a seam, by welding or fusing, or further types of joints. The drainage means are resistant to pressure. They can be inserted into a patient's body resp. led our of the patient's body via an opening of the patient's face, e.g. the mouth, the nose). A vacuum can be applied to the drainage means in a continuous or discontinuous way, the vacuum being generated e.g. by pumps or by pressure cylinders with negative pressure.

According to another embodiment, one or both end portions of the tubular hollow body can be provided, preferably surrounded, with a balloon-type component which is inflatable. The balloon-type component may be provided e.g. in addition to a funnel-shaped geometry. The balloon-type structure can be provided as an inflatable ring encompassing one or both end portions. By inflating the balloon-type component, the porous shapeable material can be sealed off from any intestinal fluids or particles.

The suction stent may comprise at least one balloon-type component which is inflatable, especially provided at the outer lateral surface of the suction stent. Preferably, the suction stent comprises two balloons, each provided at one of the end portions of the suction stent, adjacent to the porous shapeable material.

According to a further embodiment of the invention, the suction stent further comprises a biocompatible mesh or tissue, especially provided a distal end portion of the suction stent. The mesh or tissue spans resp. overstretches on of the two openings of the stent at the end portions. The mesh can be fixed to the tubular hollow body, especially at the lateral surface of the tubular hollow body, especially by an adhesive. In case a tissue is provided, the tissue should be transparent or should be provided with holes therein, in order to allow acquisition of pictures by means of an endoscope through the mesh resp. tissue.

The inventive stent can be part of a system further comprising an adapter, the stent including drainage means, wherein the adapter is arranged for coupling the drainage means to a vacuum pump and/or a Redon bottle. The adapter can be provided in the form of a tubular component with two ends which is arranged for being coupled with one end to the drainage means, and with the other end to the vacuum pump and/or the Redon bottle. Preferably, the adapter is a so called "Luer-Lock" with two or three couplings, i.e. a two-way valve or a three-way valve. A Redon bottle can be provided in the form of a reservoir for ichor.

In a preferred embodiment, the system is arranged for providing a vacuum to the drainage means via the Redon bottle. In particular, the drainage means are coupled to the Redon bottle, especially via "Luer-Lock". In the Redon bottle, there is provided an opening which can be closed, especially by a rubber plug. At the opening, the Redon bottle can be coupled with a vacuum pump. E.g., a corresponding adapter of the vacuum pump can be affixed to resp. glued on the opening. Thereby, a subnormal pressure evoked within the Redon bottle can also be exerted on the drainage means. According to an alternative, the Redon bottle itself can be used to exert the subnormal pressure, with the opening closed by the rubber plug. In other words, the suction stent can be part of a vacuum system including an adapter and a Redon bottle with an opening, the adapter being affixed to (especially glued on) the opening, wherein the adapter can be provided in the form of an adhesive connector of a vacuum wound system. The adapter can be provided in the form of an adhesive connector which can be coupled to a perforated section of a foil of a wound system.

According to one aspect, in case the suction stent has to be replaced, the drainage means can be positioned in an easy and reliable way, in particular as described in the following. In particular, the following features are applicable in context with suction stents which are positioned within the upper gastrointestinal tract. In such applications, at first, a suction tube may be positioned within the esophagus and channelled out of the body via the mouth. In such applications, the suction tube has to be channelled out of the body via the nose, especially as channelling via the mouth cannot be tolerated by the patient for a long time.

Therefore, it is provided a system for enabling introduction and rearrangement of a suction tube which is positioned within the esophagus of a patient, the system comprising a suction tube, a supplemental tube and a guide wire. The drainage means can be provided with a suction tube having a specific diameter. A supplemental tube can be provided, which is relatively short, having a length of about 25 to 35 cm, especially 30 cm, and having a diameter corresponding to the diameter of the suction tube. The supplemental tube can be connected to the suction tube via a guide wire, especially a guide wire having a length of about 35 to 45 cm, preferably 40 cm.

In a first step, the stent is positioned in an endoluminal position. Subsequently, the suction tube is channelled via the mouth. Subsequently, the supplemental tube is introduced via the nose and is channelled via the mouth. This operation can be realised quite easily. Subsequently, both tubes are connected via the guide wire and are pushed together until they contact each other. Thereby, the guide wire can be introduced in both tubes at the ends of the respective tube which protrudes out of the mouth. In a further step, the suction tube can be channelled along the guide wire and out of the body via the nose, especially by exerting a pressure force resp. a thrust on the supplemental tube. Thereby, the supplemental tube is in contact with the suction tube.

The method describes above can also be carried out during a replacement of the suction stent. Thereby, the supplemental tube (which is introduced/inserted via the nose) can be replaced by an end of the suction tube, the end of the suction tube being cut off. The end of the suction tube may remain within the nose and be cut off during removal of the drainage means.

According to a further aspect of the present invention, at least one of the above mentioned objects is attained by a method for sealing a leakage, especially an anastomosis, of a hollow organ of the human or animal body is provided, comprising the steps of:

(a) introducing a suction stent according to the present invention into the hollow organ, preferably into the gastrointestinal tract, in particular the intestine, such that the suction stent is provided with its longitudinal side at the leakage, especially in the region of the middle of the longitudinal side;

(b) providing contact between the hollow organ and the suction stent by adjusting the diameter of a porous shapeable material radially sheathing a tubular hollow body of the suction stent, the tubular hollow body being held at a fixed diameter at least in its central portion; and (c) providing, by drainage means, a subnormal pressure to the porous shapeable material such that the hollow organ is sucked resp. pressed against the porous shapeable material.

According to a preferred embodiment, an endoscope resp. catheter is introduced into the hollow organ, wherein the catheter is provided within a tube. In other words, a tube is introduced into the hollow organ, the tube including the catheter. In a second step, the catheter is removed, and the stent is compressed and introduced into the tube and pushed along the tube, especially by means of a pusher. On the pusher, there may be a mark indicating the desired position of the stent. The mark can indicate the distance resp. depth in which the stent has to be positioned within the tube. In particular, the mark indicates the distal end of the tube. In a third step, the tube is removed, wherein the pusher remains at its position within the organ. In this step, which comprises the step (b), the stent is released within the organ. As an alternative, the stent can be provided with a porous shapeable material which is compressed by a thread or filament which is wrapped round the tubular hollow body of the stent. In such a compressed state, the stent can be introduced into the organ via an endoscope resp. catheter. In a subsequent step, the thread can be removed by pulling it back, and the porous shapeable material can be released and can expand radially.

BRIEF DESCRIPTION OF THE DRAWINGS

In the following figures, the present invention is described by way of examples, wherein FIG. 1 schematically shows in a section view a suction stent according to prior art;

FIG. 3 schematically shows in a section view the suction stent according to FIG. 2;

FIG. 4 schematically shows in a cross-section view the suction stent according to FIG. 3;

FIG. 6 schematically shows in a section view a suction stent according to a further embodiment of the present invention;

DETAILED DESCRIPTION OF THE INVENTION

Figure 1:
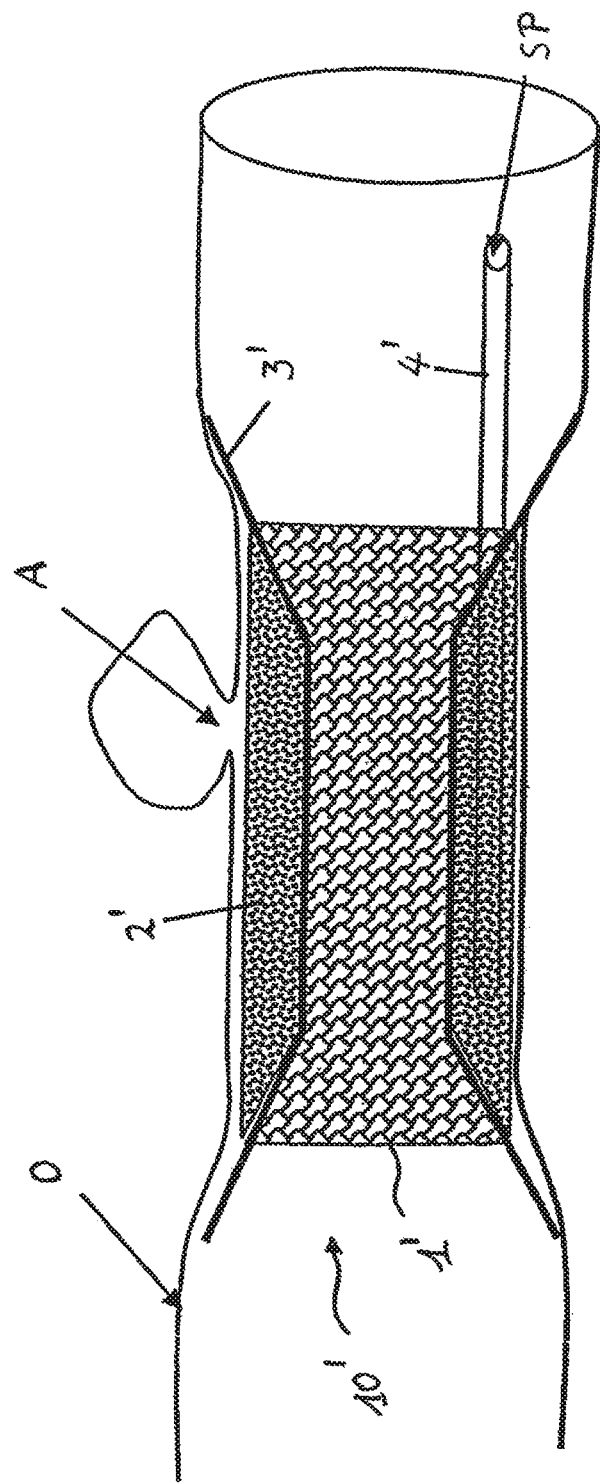

As shown in FIG. 1, a suction stent 10' is provided within a hollow organ O which has an anastomosis insufficiency A, the suction stent 10' comprising a radially expandable tubular hollow body 1' and a porous shapeable material 2' and an air- and water-tight film 3' provided between the tubular hollow body 1' and the porous shapeable material 2'. The tubular hollow body 1' is provided in the form of e.g. a stainless steel mesh. A drainage means 4' passing the air- and water-tight film 3' is provided within the porous shapeable material 2' and can be coupled e.g. to a pump for exerting a subnormal pressure SP.

Figure 2:
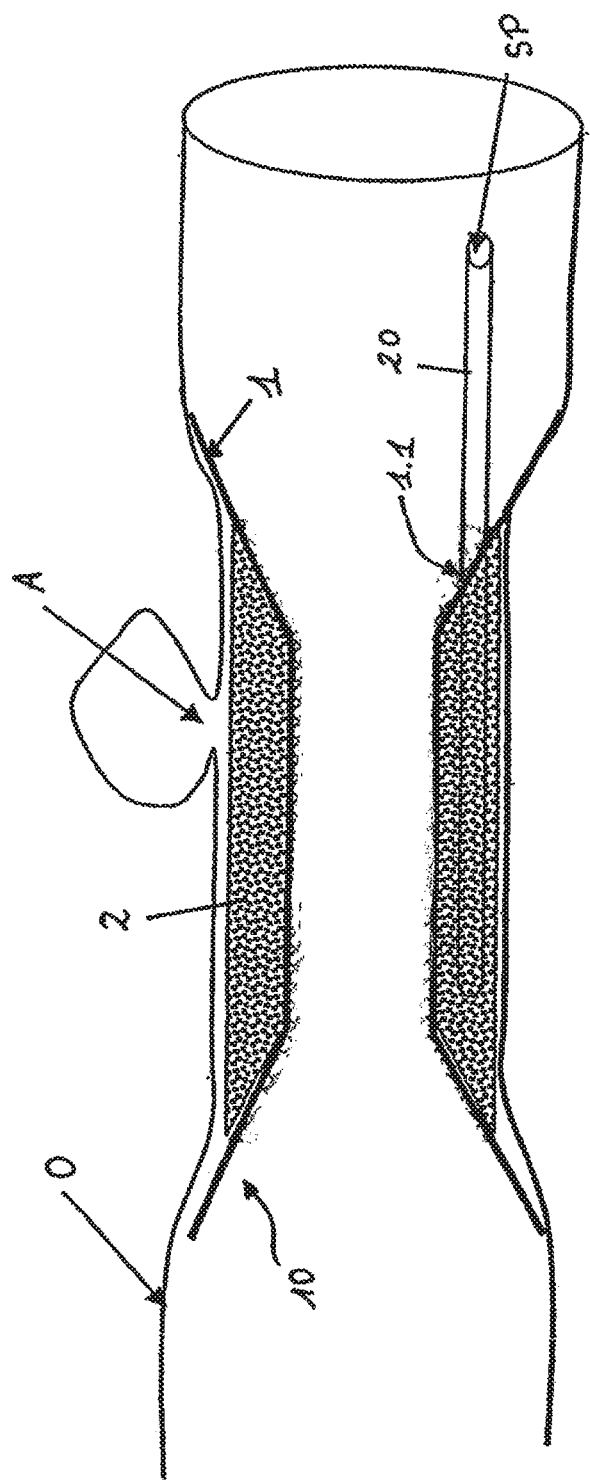
FIG. 2 schematically shows in a section view a suction stent according to an embodiment of the present invention in a position within an intestine which has an anastomosis insufficiency.

As shown in FIG. 2, a suction stent 10 is provided within a hollow organ O which has an anastomosis insufficiency A, the suction stent 10 comprising an incompressible and an air- and water-tight tubular hollow body 1 and a porous shapeable material 2 provided on the outer surface of the tubular hollow body 1. Drainage means 20 passing through the tubular hollow body 1 in a point of passage 1.1 are provided within the porous shapeable material 2, and they can be coupled e.g. to a pump for exerting a subnormal pressure SP.

In FIG. 3, the suction stent 10 according to FIG. 2 is shown without resp. separated from the hollow organ. The tubular hollow body 1 comprises a central portion 1a and two end portions 1b, the central portion 1a being incompressible/not extendable in the radial direction, and the end portions 1b being radially extendable or rigid. Both end portions 1b are provided in a funnel-shaped geometry. In this embodiment, the maximum outer diameter of the tubular hollow body 1 is greater or equal than the maximum outer diameter of the porous shapeable material 2. The funnel-shaped geometry at both end portions 1b of the tubular hollow body 1 can ensure that the faces resp. front sides 2a of the porous shapeable material 2 do not need to be sealed for air- and/or water-tightness; the tubular hollow body 1 itself can ensure air- and/or water-tightness, also with respect to the longitudinal direction. Thereby, any danger of intestinal secretions occluding the porous shapeable material can be reduced.

The porous shapeable material 2 can optionally be provided with the same diameter as the tubular hollow body 1, as suggested by the dotted portion surrounding the porous shapeable material 2.

As shown in FIG. 4, the porous shapeable material 2 is arranged annularly around the tubular hollow body 1.

Figure 5A:
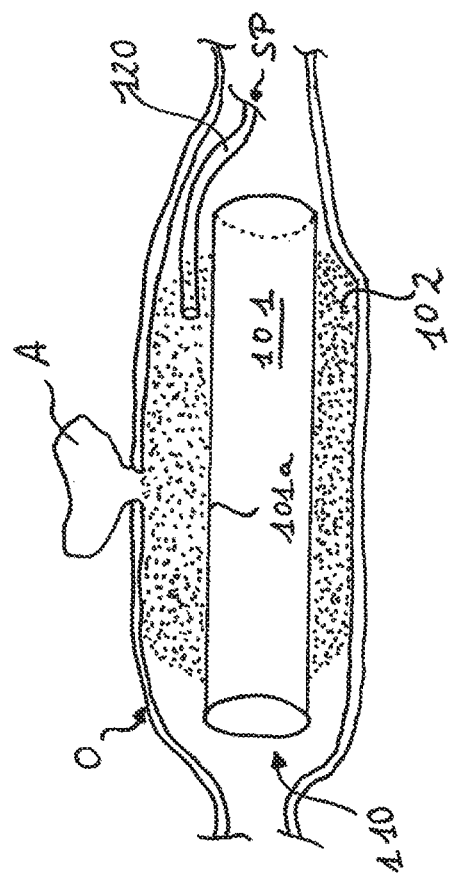
FIG. 5a schematically shows in a section view a suction stent according to a further embodiment of the present invention in a position within an intestine which has an anastomosis insufficiency.
Figure 5B:
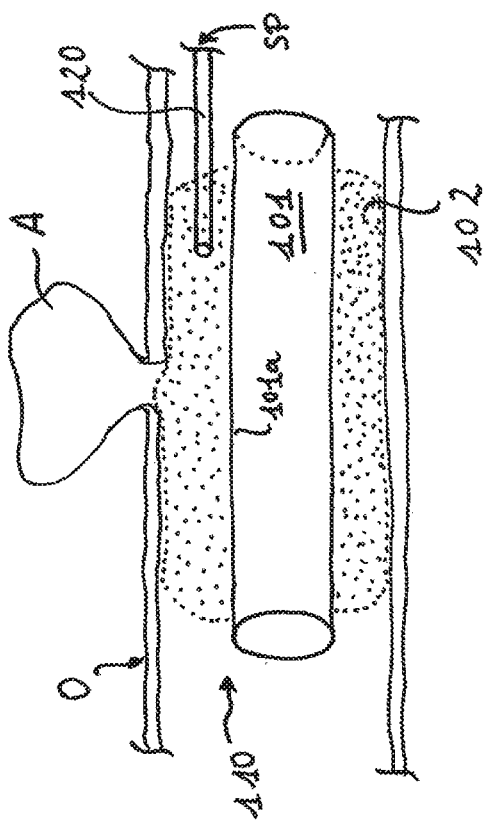
FIG. 5b schematically shows the suction stent according to FIG. 5a, wherein a subnormal pressure is applied to the intestine resp. the stent.

As shown in FIGS. 5a and 5b, a suction stent 110 is provided within a hollow organ O (e.g. the intestine) which has an anastomosis insufficiency A, the suction stent 110 comprising an incompressible and an air- and water-tight tubular hollow body 101 as well as a porous shapeable material 102 provided on the outer surface of the tubular hollow body 101. The tubular hollow body 101 is provided with a central portion 101a which extends along the same length of the tubular hollow body 101 as the porous shapeable material 102. Drainage means 120 passing through the tubular hollow body 101 are provided within the porous shapeable material 102, and they can be coupled e.g. to a pump for exerting a subnormal pressure SP. In FIG. 5a, a subnormal pressure SP is not applied yet. The suction stent 110 is positioned at least approximately centered with respect to the anastomosis insufficiency A, and the porous shapeable material 102 has snuggled to the inner wall of the hollow organ O. In FIG. 5b, the subnormal pressure SP has been applied, and the (inner) wall of the hollow organ O follows the outer contour of the porous shapeable material 102. With respect to FIG. 5a, the diameter of the porous shapeable material 102 is slightly reduced, as the organ O exerts a pressure on the porous shapeable material 102. The diameter of the tubular hollow body 101 remains the same, independently of any subnormal pressure.

In FIG. 6, a suction stent 210 is provided with an incompressible and an air- and water-tight tubular hollow body 201 as well as a porous shapeable material 202 provided on the outer surface of the tubular hollow body 201. The tubular hollow body 201 is provided with a central portion 201a which has a constant inner luminal diameter d1, the diameter d1 being fixed resp. predefined, especially by the characteristics of an incompressible material of the tubular hollow body 201, and the central portion 201a extends along the full length of the tubular hollow body 201. The suction stent 210 resp. the porous shapeable material 202 has a variable resp. adaptable outer diameter d2. The (variable) thickness of the porous shapeable material 202 is indicated by the reference sign d3. The overall length of the suction stent 210, especially of the tubular hollow body 201, is indicated by reference sign L. In this embodiment, the porous shapeable material 202 is provided along the full length L of the stent 210. Drainage means are not shown.

Figure 7:
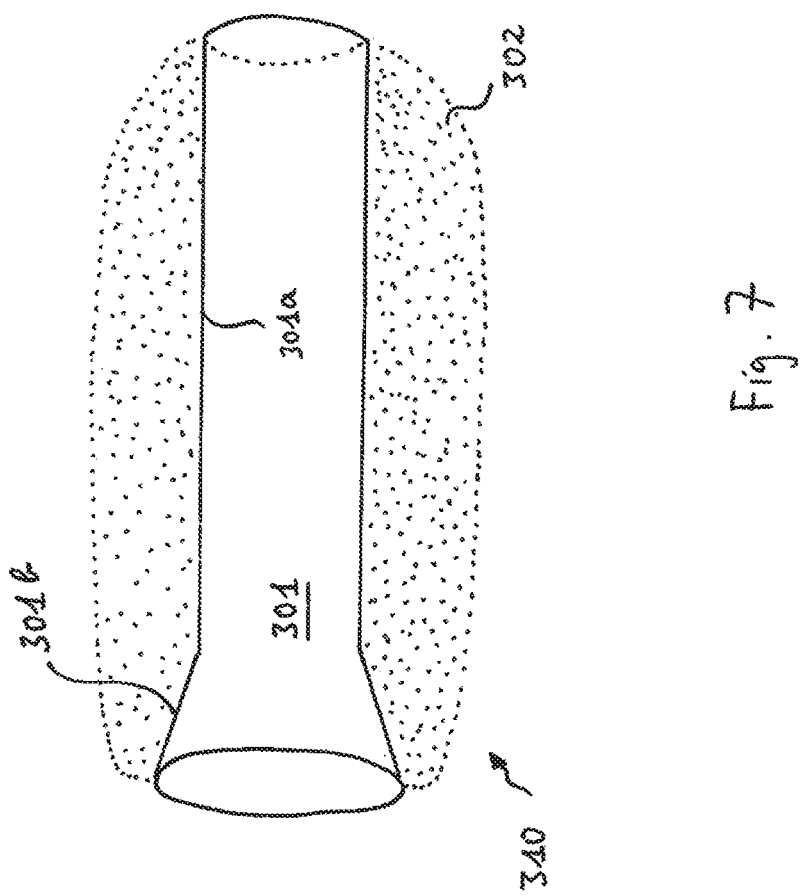
FIG. 7 schematically shows in a section view a suction stent according to a further embodiment of the present invention.

In FIG. 7, a suction stent 310 is provided with an incompressible and an air- and water-tight tubular hollow body 301 as well as a porous shapeable material 302 provided on the outer surface of the tubular hollow body 301, wherein the tubular hollow body 301 has a central portion 301a and one end portion 301b with a funnel-shaped geometry. At the end portion 301b, the porous shapeable material 302 has an outer diameter which corresponds to the outer diameter at the section of the central portion 301a, at least approximately. Thereby, it can be ensured that a pressure directed radially inwards can be damped by the porous shapeable material 302 such that an inner wall of a hollow organ does not get in contact with the tubular hollow body 301. The funnel-shaped geometry can facilitate the flow of a medium resp. fluid through the tubular hollow body 301. The further end portion is provided with a cylindrical geometry. Drainage means are not shown.

Figure 8:
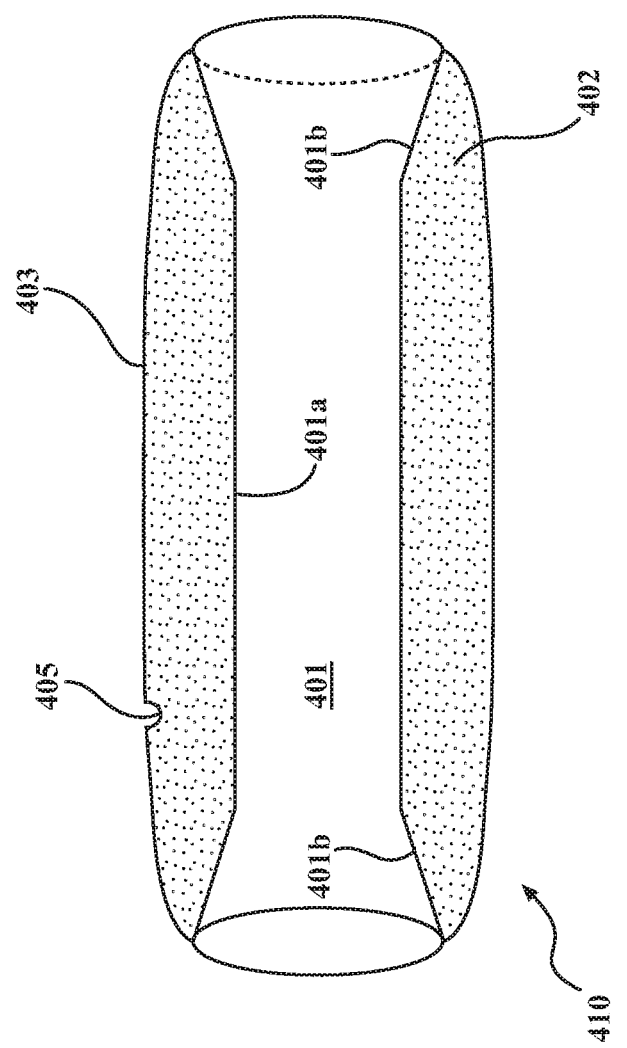
FIG. 8 schematically shows in a section view a suction stent according to a further embodiment of the present invention.

In FIG. 8, a suction stent 410 provided with an incompressible and an air- and water-tight tubular hollow body 401 as well as a porous shapeable material 402 provided on the outer surface of the tubular hollow body 401 is shown, wherein the tubular hollow body 401 has a central portion 401a and two end portions 401b with a funnel-shaped geometry. At the end portions 401b, the porous shapeable material 402 has an outer diameter which corresponds to the outer diameter at the section of the central portion 401a, at least approximately. Further, the stent 410 comprises a foil 403 which is arranged at the outer surface of the porous shapeable material 402. The foil 403 can ensure that any danger of reaction between the porous shapeable material 402 and an organ, e.g. allergic reactions, can be excluded, irrespective of the material of the porous shapeable material 402. There may be perforations 405 in the foil 403.

Figure 9:
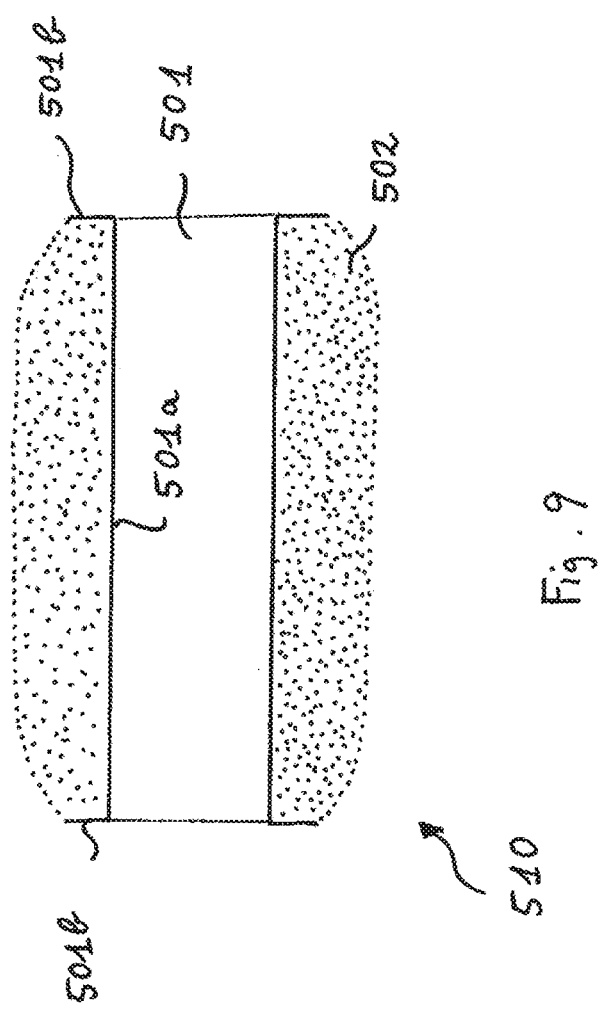
FIG. 9 schematically shows in a section view a suction stent according to a further embodiment of the present invention.

In FIG. 9, a suction stent 510 provided with an incompressible and an air- and water-tight tubular hollow body 501 as well as a porous shapeable material 502 provided on the outer surface of the tubular hollow body 501 is shown, wherein the tubular hollow body 501 has a central portion 501a and two flange-like end portions 501b extending radially outwardly. At the end portions 501b, the porous shapeable material 502 has an outer diameter which corresponds to the maximum outer diameter the end portions 501b. Thereby, the end portions 501b can seal the porous shapeable material 502 with respect to the longitudinal direction, i.e. the faces resp. front sides of the porous shapeable material 502. The end portions 501b can ensure air- and/or water-tightness.

The features of the embodiments shown in FIGS. 2, 5a, and 6 to 9 can be combined with each other. They are interchangeable.

Figure 10:
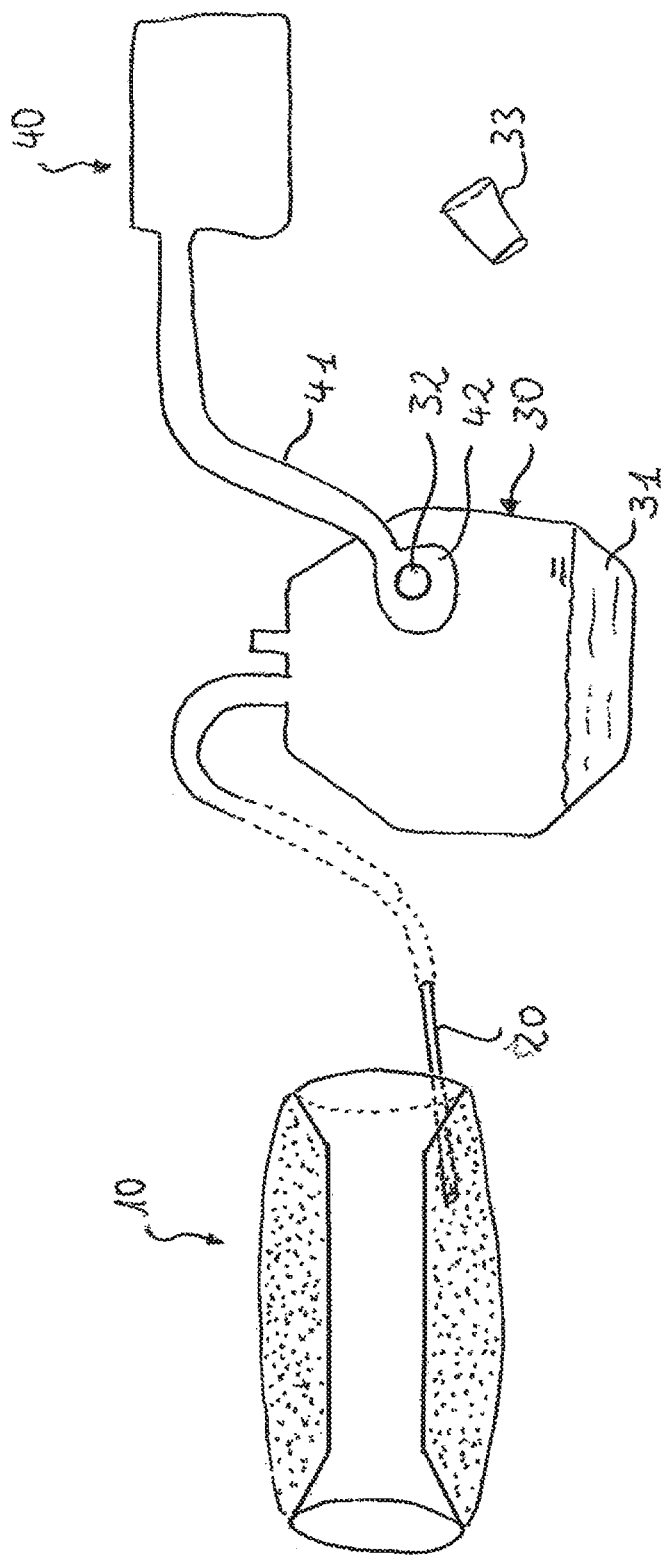
FIG. 10 schematically shows in a side view resp. section view a vacuum system and a redon bottle and a suction stent according to one embodiment of the present invention.

FIG. 10 shows a vacuum system for providing a universal interface between a suction stent and a vacuum pump. Drainage means 20 of a suction stent 10 are coupled to a Redon bottle 30. In the Redon bottle 30, a fluid 31 is collected which is stored at the bottom of the bottle 30. The fluid 30 had been sucked from a patient. In the Redon bottle 30, there is provided an opening 32 which can be closed by a rubber plug 33. At the opening 32, the Redon bottle 30 can be coupled with a vacuum system 40, especially via a vacuum tube 41. The Redon bottle 30 may be closed by the rubber plug 33 in case no vacuum system 40 is coupled to the Redon bottle 30. For coupling the vacuum system 40 to the Redon bottle 30, a corresponding adapter 42 of the vacuum system 40 resp. the vacuum tube 41 can be affixed to the opening 32, especially glued on the opening 32. Thereby, a subnormal pressure evoked within the Redon bottle 30 is exerted on the drainage means 20 and the suction stent 10. The adapter 42 can be provided in the form of a connector of a vacuum wound system. The adapter 42 can be glued on a perforated section of a foil of a wound system. Thereby, an universal adapter is provided which can be affixed in conjunction with any vacuum system available (with any commonly used vacuum system) in an easy and reliable way, especially via an adhesive connection which is usually provided for connecting the vacuum system to a foil of a wound system.

Figure 11:
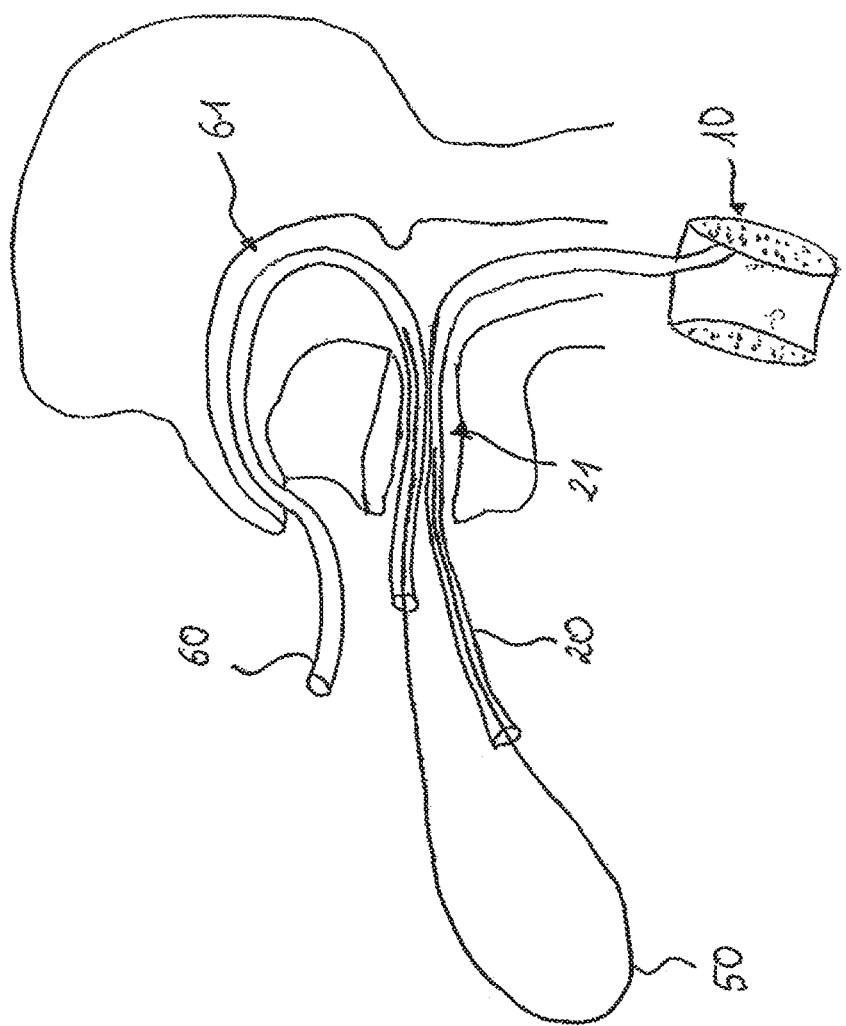
FIG. 11 schematically shows in a side view a system enabling introduction and rearrangement of a suction tube in conjunction with a suction stent according to one embodiment of the present invention.

FIG. 11 shows a system for enabling introduction and rearrangement of a suction tube 20 which is positioned within the nose of a patient, the system comprising the suction tube 20, a supplemental tube 60 and a guide wire 50. Such a system can be used e.g. in conjunction with suction stents which are positioned within the upper gastrointestinal tract, especially within the esophagus. The supplemental tube 60 can be provided with a relatively short length, especially a length of about 25 to 35 cm, especially 30 cm, and with a diameter preferably corresponding to the diameter of the suction tube 20. In particular, the inner diameter of the supplemental tube 60 corresponds to the inner diameter of the suction tube 20. The supplemental tube 60 can be coupled with the suction tube 20 via the guide wire 50, especially a guide wire having a length of about 35 to 45 cm, preferably 40 cm.

In a first step, a suction stent 10 is positioned in an endoluminal position, wherein the suction stent 10 is coupled to the suction tube 20 resp. to drainage means. Thereby, the suction tube 20 is channelled via the mouth 21. Subsequently, the supplemental tube 60 is introduced via the nose and is channelled via the mouth 21. The channelling of the supplemental tube 60 via the mouth can be realized quite easily. Then, the guide wire 50 is introduced into both tubes 20, 60 at the ends of the tubes 20, 60 which protrude out of the mouth 21. In particular, the guide wire 50 is introduced into each tube 20, 60 along a length of at least 15 cm, preferably at least 20 cam, in order to ensure reliability and stability of the arrangement. According to one embodiment, the guide wire is introduced into the supplemental tube 60 along its full length or even protrudes out of the supplemental tube 60. A guide wire 50 being arranged such that it protrudes out of the supplemental tube 60 can ensure that the position of the guide wire 50 relative to the supplemental tube 60 can be controlled easily. Thereby, both tubes 20, 60 are connected via the guide wire 50. In a further step, both tubes 20, 60 can be pushed together until they contact each other. In particular, the supplemental tube 60 is displaced along the guide wire 50 until it contacts the front side resp. free end of the suction tube 20 with its front side. A vacuum pump can be coupled to the supplemental tube 60, in particular once the supplemental tube 60 is in contact with the suction tube 20. In a further step, the suction tube 20 can be channelled along the guide wire 60 and out of the body via the nasal cavity 61, especially by exerting a pressure force resp. a thrust on the supplemental tube 60. Thereby, the supplemental tube 60 is in contact with the suction tube 20. A subnormal pressure can be applied to both tubes, in particular in order to maintain contact between both tubes 20, 60. In such a way, a suction tube 20 which had been introduced via the mouth 21 can be channelled out via the nose in an easy way and with little effort. Once the suction tube 20 is channelled out via the nose, the guide wire 50 can be removed.

Figure 12B:
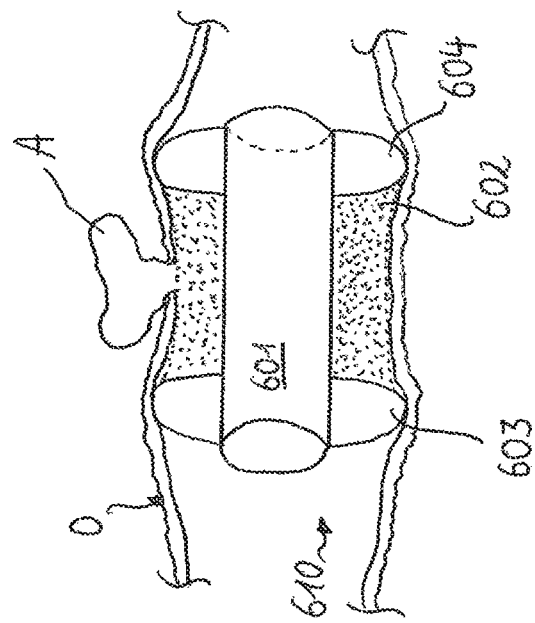
FIG. 12b schematically shows the suction stent according to FIG. 11a, wherein a subnormal pressure is applied to the intestine resp. the stent.
Figure 12A:
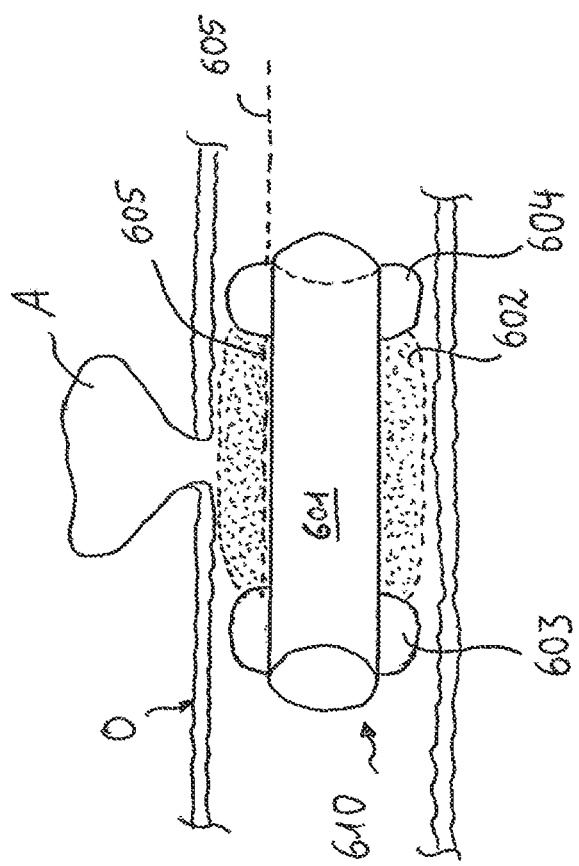
FIG. 12a schematically shows in a section view a suction stent according to a further embodiment of the present invention in a position within an intestine which has an anastomosis insufficiency.

FIG. 12a shows a suction stent 610 which is provided within a hollow organ O (e.g. the intestine) which has an anastomosis insufficiency A, the suction stent 610 comprising an incompressible and an air- and water-tight tubular hollow body 601 as well as a porous shapeable material 602 provided on the outer surface of the tubular hollow body 601. A first balloon 603 and a second balloon 604 are arranged at the outer surface of the tubular hollow body 601 adjacent to the porous shapeable material 602. The balloons 603, 604 are shown in a section view, but not the tubular hollow body 601. The balloons 603, 604 constitute a balloon-type component of the stent 610 and are fixed on the outer surface, e.g. by an adhesive. Optionally, the porous shapeable material 602 can (also) be fixed at an inner face resp. inner lateral side of each of the balloons 603, 604, e.g. by an adhesive. The balloons 603, 604 are positioned at a respective end of the tubular hollow body 601.

The balloons 603, 604 are inflatable, especially via a kind of conduit 605 which is schematically shown in FIG. 12a. The conduit 605 can have two separate branches resp. parts, each connected to one of the balloons 603, 604. With such a configuration, each balloon 603, 604 can be inflated individually. Preferably, the conduit 605 is connected to a "Luer Lock" tube system or the conduit 605 constitutes a part of such a "Luer Lock" tube system. The "Luer Lock" tube system has an access point for manually inflating the balloons, especially with a predetermined volume of air. For example, the access point can be provided in the form of an adapter for an injection device which can be coupled with the "Luer Lock" system. The injection device resp. shot can be provided with a defined volume, e.g. 10-20 ml. With such a system, the balloons can be inflated manually without any danger of excess pressure within the balloons or within the intestine. As an alternative, the conduit 605 may be connected to a control unit (not shown) which is configured for adjusting the pressure within the balloons.

By inflating the balloon-type component, the porous shapeable material 602 can be sealed off from any intestinal fluids or particles. Also, the stent 610 can be positioned within the intestine in an exact position more reliably, reducing the danger of any dislocation. Also, the balloon-type component 603, 604 can ensure a subnormal pressure to be applied more effectively to the intestine resp. the porous shapeable material 602. The balloons 603, 604 can be made of silicone material or of an alternative plastic or synthetic material which is biocompatible.

As shown in FIG. 12a, the balloons 603, 604 are not inflated yet, or they are only partially inflated. The outer diameter of the balloons 603, 604 is about the same or is slightly smaller than the outer diameter of the porous shapeable material 602, which is shown in an expanded state.

In FIG. 12b, the balloons 603, 604 have been inflated and are in contact with the (inner) wall of the hollow organ O. The outer diameter of the balloons 603, 604 is bigger than the outer diameter of the porous shapeable material 602. With respect to FIG. 12a, the diameter of the porous shapeable material 602 is slightly reduced.

Preferably, the balloons 603, 604 can be inflated prior to applying a subnormal pressure to the porous shapeable material 602 by drainage means (not shown). Thus, a contact between the intestine and the stent 610 can be established, and the axial position of the stent 610 with respect to the anastomosis A can be defined. In a second step, the subnormal pressure can be applied. The inner wall of the intestine can be sucked against the outer surface of the porous shapeable material 602. Thus, it can effectively be prevented that any intestinal fluids or particles get in contact with the porous shapeable material 602.

The embodiment shown in FIG. 12a can be combined with any feature of the further embodiments shown in the FIG. 2, 5a, 6 to 9, 13 or 14.

Figure 13:
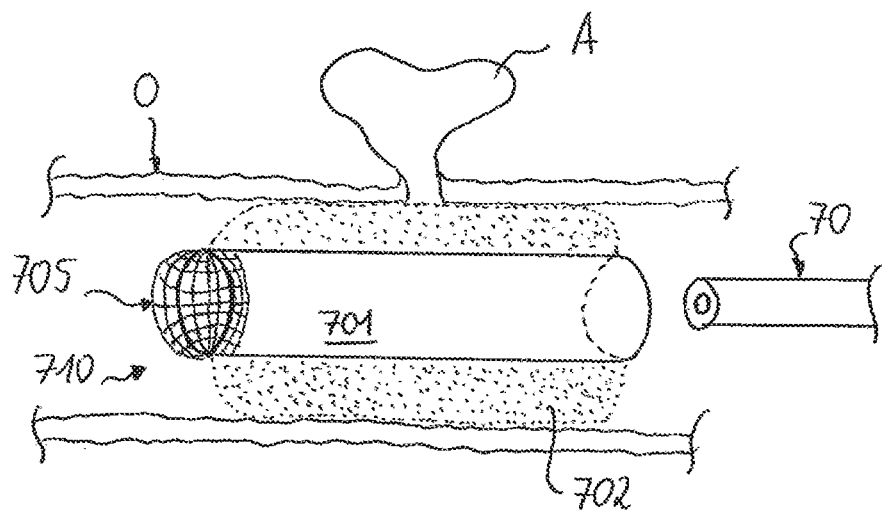
FIG. 13 schematically shows in a section view a suction stent according to a further embodiment of the present invention in a position within an intestine which has an anastomosis insufficiency.

FIG. 13 shows a suction stent 710 which is provided within a hollow organ O (e.g. the intestine) which has an anastomosis insufficiency A, the suction stent 710 comprising an incompressible and an air- and water-tight tubular hollow body 701 as well as a porous shapeable material 702 provided on the outer surface of the tubular hollow body 701. At the distal (anterior) end resp. end portion of the tubular hollow body 701, a kind of porous tissue, web, mesh or meshwork 705 is provided. The mesh 705 can be provided with a structure like a fishnet for example. The mesh 705 can be made of e.g. polypropylene or of an alternative plastic or synthetic material which is biocompatible. The mesh 705 is fixed at the tubular hollow body 701, especially at an outer surface of the tubular hollow body 701, e.g. by an adhesive. The mesh 705 can ensure that the stent 710 can be positioned by means of an endoscope 70, especially during acquisition of images of the intestine, in order to correctly position the stent 710 with respect to the anastomosis A. The endoscope 70 may push forward the stent 710 in a distal direction by exerting a pressure resp. force on the mesh 705 in an axial, distal direction. The mesh opening of the mesh 705 is smaller than the diameter of a distal tip of the endoscope 70. Thereby, the mesh 705 can ensure that a distal end portion of the stent 710 is positioned at the same or at least approximately the same axial position as the distal end of the endoscope 70. Once the anastomosis A is visible (by means of the endoscope 70), the endoscope 70 may be pushed further in the distal direction for a length corresponding to about the half of the length of the stent 710, in order to position the stent 710 centrically with respect to the anastomosis A.

After having inserted and positioned the stent within the intestine, the mesh 705 can be cut by endoscopic scissors which may be passed within the tubular hollow body 701 of the stent 710. The endoscopic scissors may be passed via any working channel resp. lumen of the endoscope 70. This method of positioning the stent 710 may also be carried out in case the stent 710 is provided within any system or shell or envelope or enclosure for facilitating insertion of the stent.

The embodiment shown in FIG. 13 can be combined with any feature of the further embodiments shown in the FIG. 2, 5a, 6 to 9, 12a or 14.

Figure 14:
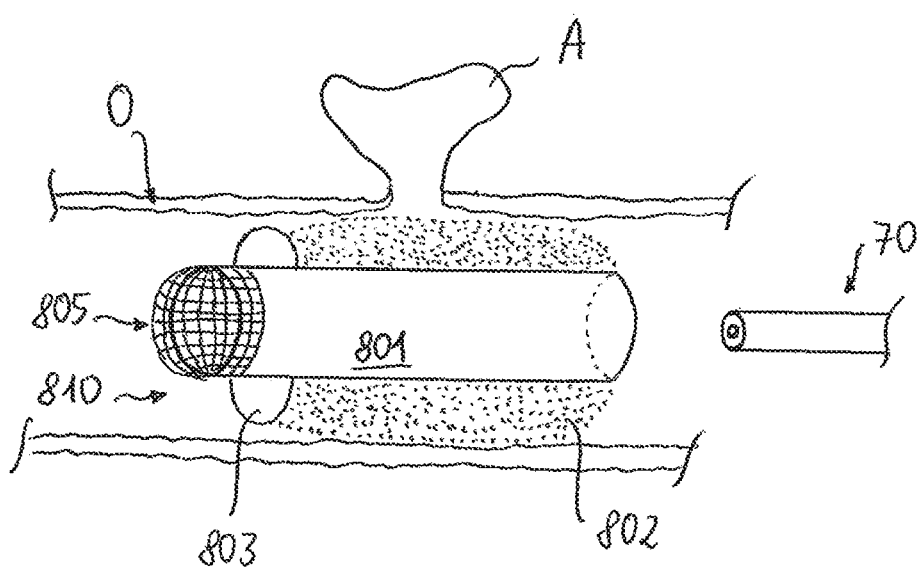
FIG. 14 schematically shows in a section view a suction stent according to a further embodiment of the present invention in a position within an intestine which has an anastomosis insufficiency.

FIG. 14 shows a suction stent 810 which is provided within a hollow organ O (e.g. the intestine) which has an anastomosis insufficiency A, the suction stent 810 comprising an incompressible and an air- and water-tight tubular hollow body 801 as well as a porous shapeable material 802 provided on the outer surface of the tubular hollow body 801. At the distal (anterior) end resp. end portion of the tubular hollow body 801, a kind of porous tissue, web, mesh or meshwork 805 is provided. Further, the stent 810 comprises an inflatable balloon 803 which is fixed at an outer lateral side of the tubular hollow body 801. The stent 810, the mesh 805 and the balloon 803 may have the same characteristics as mentioned in context with the FIGS. 12a, 12b and 13.

The embodiment shown in FIG. 14 can be combined with any feature of the further embodiments shown in the FIG. 2, 5a, 6 to 9, 12a or 13.

The invention claimed is:

1. A method for sealing a leakage of a hollow organ of a human or animal body, comprising the steps of:
    (a) providing an endoscope or catheter with a tube;
    (b) introducing the endoscope or catheter into the hollow organ such that the tube is introduced into the hollow organ; and
    (c) introducing a suction stent through the tube into the hollow organ such that the suction stent is provided with its longitudinal side at the leakage, the suction stent having a tubular hollow body and, at least a central portion of the tubular hollow body having a fixed diameter and not being expandable, the suction stent further having a porous shapeable material radially sheathing the tubular hollow body in at least a section of the tubular hollow body;
    whereby the suction stent seals the leakage.

2. The method of claim 1, wherein:
    the tubular hollow body is open in a longitudinal direction and made of biocompatible material; and
    the porous shapeable material is biocompatible and shapeable in a radial direction.

3. The method of claim 1, wherein the tubular hollow body is a pipe or tube which is flexible with respect to a longitudinal axis of the tubular hollow body.

4. The method of claim 1, wherein the porous shapeable material is provided along at least 50% of the tubular hollow body in its longitudinal direction.

5. The method of claim 1, wherein the tubular hollow body is impermeable to water or to water and gas.

6. The method of claim 1, wherein the tubular hollow body is radially expandable in a peripheral portion of the tubular hollow body.

7. The method of claim 1, wherein the tubular hollow body is entirely made of an inexpandable material.

8. The method of claim 1, wherein a thickness of the porous shapeable material in a discharged state is between 4 and 12 mm.

9. The method of claim 1, wherein a luminal inner diameter of the tubular hollow body is between 5 and 15 mm.

10. The method of claim 1, wherein an outer diameter of the porous shapeable material in a discharged state is between 15 and 35 mm.

11. The method of claim 1, wherein a ratio of an outer diameter of the porous shapeable material in a discharged state to a luminal inner diameter of the tubular hollow body is between 3 and 7.

12. The method of claim 1, wherein the suction stent further comprises a drain, a suction hose, or a vacuum tube, which is fixed at or in the porous shapeable material.

13. The method of claim 1, wherein the suction stent further comprises at least one balloon-type component which is inflatable.

14. The method of claim 1, wherein the suction stent further comprises a biocompatible mesh or tissue.

15. The method of claim 1, wherein the porous shapeable material is formed as an open-pored structure and has a relieved state and a compressed state, a diameter of the porous shapeable material in the relieved state being greater than in the compressed state.

16. The method of claim 15, wherein the open-pored structure has 20-40 pores per inch.

17. The method of claim 1, wherein
    the tubular hollow body is radially expandable in a peripheral portion of the tubular hollow body.

18. The method of claim 1, wherein the tubular hollow body has a funnel-shaped geometry in a peripheral portion of the tubular hollow body.

19. The method of claim 1, wherein at least part of the porous shapeable material radially sheathing the tubular hollow body is sealed to ensure air- and/or water-tightness.

20. The method of claim 19, wherein one or both end portions of the porous shapeable material is/are sealed to ensure air- and/or water-tightness.

21. The method of claim 1, further comprising:
    providing, by a drain, a subnormal pressure to the porous shapeable material such that the hollow organ is sucked against the porous shapeable material.

22. The method of claim 1, further comprising providing a pusher, the step of introducing the suction stent through the tube comprising pushing the suction stent through the tube with the pusher, the pusher having a mark indicating a desired position of the stent.

23. The method of claim 1, wherein the hollow organ is a gastrointestinal tract.

24. A method for sealing a leakage of a hollow organ of a human or animal body, comprising the steps of:
    (a) providing an endoscope or catheter with a tube;
    (b) introducing the endoscope or catheter into the hollow organ such that the tube is introduced into the hollow organ;
    (c) compressing a suction stent;
    (d) introducing the compressed suction stent through the tube into the hollow organ such that the suction stent is provided with its longitudinal side at the leakage, the suction stent having a tubular hollow body and, at least a central portion of the tubular hollow body having a fixed diameter and not being expandable, the suction stent further having a porous shapeable material radially sheathing the tubular hollow body in at least a section of the tubular hollow body;
    whereby the suction stent seals the leakage.

25. The method of claim 24, wherein the step of compressing the suction stent comprises compressing the porous shapeable material by a thread or filament wrapped around the tubular hollow body of the stent, the method further comprising releasing and radially expanding the porous shapeable material by removing the thread or filament after the stent is introduced into the hollow organ.

* * * * *